United States Patent [19]

Naughton et al.

[11] Patent Number: 5,842,477
[45] Date of Patent: Dec. 1, 1998

[54] METHOD FOR REPAIRING CARTILAGE

[75] Inventors: Gail K. Naughton, Del Mar; Jane Willoughby, Solana Beach, both of Calif.

[73] Assignee: Advanced Tissue Sciences, Inc., La Jolla, Calif.

[21] Appl. No.: 604,284

[22] Filed: Feb. 21, 1996

[51] Int. Cl.$^6$ ................................ A61B 19/00; A61F 2/08
[52] U.S. Cl. ................................ 128/898; 623/11; 623/13
[58] Field of Search ........................ 623/11, 13; 128/898

[56] References Cited

U.S. PATENT DOCUMENTS

| | | |
|---|---|---|
| 4,520,821 | 6/1985 | Schmidt et al. . |
| 4,609,551 | 9/1986 | Caplan et al. . |
| 4,846,835 | 7/1989 | Grande . |
| 4,963,489 | 10/1990 | Naughton et al. . |
| 5,032,508 | 7/1991 | Naughton et al. . |
| 5,041,138 | 8/1991 | Vacanti et al. . |
| 5,160,490 | 11/1992 | Naughton et al. . |
| 5,197,985 | 3/1993 | Caplan et al. . |
| 5,226,914 | 7/1993 | Caplan et al. . |
| 5,266,480 | 11/1993 | Naughton et al. . |
| 5,376,118 | 12/1994 | Kaplan et al. ............................ 623/13 |
| 5,443,950 | 8/1995 | Naughton et al. . |
| 5,460,959 | 10/1995 | Mulligan et al. .................... 435/172.3 |
| 5,478,739 | 12/1995 | Slivka et al. ............................. 623/15 |
| 5,510,254 | 4/1996 | Naughton et al. . |
| 5,512,475 | 4/1996 | Naughton et al. . |
| 5,516,681 | 5/1996 | Naughton et al. . |
| 5,518,915 | 5/1996 | Naughton et al. . |
| 5,541,107 | 7/1996 | Naughton et al. . |
| 5,723,331 | 3/1998 | Tubo et al. .............................. 623/11 |

FOREIGN PATENT DOCUMENTS

WO 93/15694   8/1993   WIPO .

OTHER PUBLICATIONS

Gallay, S. et al., 1994, "Relationship of Donor Site to Chondrogenic Potential of Periosteum In Vitro", J of Orthopaedic Research 12:515–525.
Kreder, H. et al., 1994, "Biologic Resurfacing of a Major Joint Defect With Cryopreserved Allogenic Periosteum Under the Influence of Continuous Passive Motion in a Rabbit Model", Clinical Orthopedics and Related Research 300:288–296.
Ritsilä, V. et al., 1994, "Periosteal and Perichondral Grafting in Reconstructive Surgery", Clinical Orthopedics and Related Research 302:259–265.
Argün, M. et al., 1993, "The Chondrogenic Potential of Free Autogenous Periosteal and Fascial Grafts for Biological Resurfacing of Major Full–Thickness Defects in Joint Surfaces (An Experimental Investigation in the Rabbit)", Tokai J Exp Clin Med 18:107–116.
Nakase, T. et al., 1993, "Clonal Analysis for Developmental Potential of Chick Periosteum–Derived Cells: Agar Gel Culture System", Biochem Biophys Res Commun 195:1422–1428.
Bruns J. et al., 1992, "The Rib Perichondrium", Acta Anat 144:258–266.

Coutts, R. et al., 1992, "Rib Periochondrial Autografts in Full–Thickness Articular Cartilage Defects in Rabbits", Clinical Orthopedics and Related Research 275:263–273.
de Tulio, S. et al., 1992, "Fresh Autogenous Rib Cartilage Graft to the Malar Process of Rats with and without Removal of the Perichondrium: A Histological Study", J Nihon Univ Sch Dent 34:8–15.
Izumi, T. et al., 1992, "Transforming Growth Factor $\beta_1$ Stimulates Type II Colagen Expression in Cultured Periosteum–Derived Cells", J of Bone and Mineral Research 7:115–121.
Naughton, B. et al., 1992, "Long–Term Expression of a Retrovirally Introduced β–Galactosidase Gene in Rodent Cells Implanted In Vivo Using Biodegradable Polymer Meshes", Som Cell and Mol Genetics 18:451–462.
Tsai, C. et al., 1992, "Meniscal Repair with Autogenous Periosteum and Fibrin Adhesive System", Chin Med J (Taipei) 49:170–176.
Tsai, C. et al., 1992, "Preliminary Study of Cartilage Repair with Autologous Periosteum and Fibrin Adhesive System", J Formosan Med Assoc 91:S239–245.
Korkala O. and Kuokkanen, H., 1991, "Autogenous Osteoperiosteal Grafts in the Reconstruction of Full–thickness Joint Surface Defects", Int Orthop (SICOT) 15:233–237.
Nakahara, H. et al., 1991, "Culture–Expanded Human Periosteal–Derived Cells Exhibit Osteochondral Potential In Vivo", J of Orthopedic Res 9:465–476.
Vachon, A. et al., 1991, "Biochemical Study of Repair of Induced Osteochondral Defects of the Distal portion of the Radial Carpal Bone in Horses by Use of Periosteal Autografts", Am J Vet Res 52:328–332.
Bulstra, S. et al., 1990, "The Potential of Adult Human Perichondrium to Form Hyalin Cartilage In Vitro", J of Orthopedic Research 8:328–335.
Homminga G. et al., 1990, "Perichondral Grafting for Cartilage Lesions of the Knee", J of Bone and Joint Surgery 72:1003–1007.

(List continued on next page.)

Primary Examiner—Paul B. Prebilic
Attorney, Agent, or Firm—Pennie & Edmonds LLP

[57] ABSTRACT

The present invention relates to methods of making and/or repairing cartilage in vivo comprising implanting into a patient, at a site of cartilage damage or loss, a biocompatible, non-living three-dimensional scaffold or framework structure in combination with periosteal/perichondrial tissue that can be used to hold the scaffold in place and provides a source of chondrocyte progenitor cells, chondrocytes and other stromal cells for attachment to the scaffold in vivo. In addition, a preparation of cells that can include chondrocytes, chondrocyte progenitor cells or other stromal cells is administered, either before, during or after implantation of the scaffold and/or the periosteal perichondrial tissue; the cells are administered directly into the site of the implant in vivo and promote the induction of factors that enhance chondrogenesis and the migration of chondrocytes, progenitor cells and other stromal cells from the adjacent in vivo environment into the scaffold for the production of new cartilage at the site of implantation.

48 Claims, No Drawings

OTHER PUBLICATIONS

Nakahara, S. et al., 1990, "Bone and Cartilage Formation in Diffusion Chambers by Subcultured Cells Derived from the Periosteum", Bone 11:181–188.

Skoog, V. et al., 1990, "The Effect of Growth Factors and Synovial Fluid on Chondrogenesis in Perichondrium", Scand J Plast Reconstr Hand Surg 24:89–95.

Verwoerd, C. et al., 1990, "Wound Healing of the Nasal Septal Perichondrium in Young Rabbits", ORL 52:180–186.

Zarnett, R. and Salter, R., 1989, "Periosteal Neochondrogenesis for Biologically Resurfacing Joints: Its Cellular Origin", CJS 32:171–174.

Brittberg et al., "Treatment of Deep Cartilage Defects in the Knee with Autologous Chondrocyte Transplantation", *The New England Journal of Medicine,* 331(14):889–895 (1994).

Wakitani et al., "Mesenchymal Cell–Based Repair of Large, Full–Thickness Defects of Articular Cartilage", *The Journal of Bone and Joint Surgery,* 76–A(4):579–592 (1994).

O'Driscoll et al., "Chondrogensis in Periosteal Explants", *The Journal of Bone and Joint Surgery,* 76–A(7):1042–1051 (1994).

K. Messner, "Meniscal substitution with a Teflon–periosteal composite graft: a rabbit experiment", *Biomaterials,* 15(3):223–230 (1994).

Bean et al., "Reconstruction of the Anterior Laryngeal Wall with a Composite Graft of Demineralized Bovine Bone Matrix and Autogenous Perichondrium", *ORL,* 56:224–229 (1994).

Taniguchi et al., "Transforming Growth Factor β1–Induced Cellular Heterogeneity in the Periosteum of Rat Parietal Bones", *Calcif Tissue Int,* 53:122–126 (1993).

K. Messner and J. Gillquist, "Synthetic implants for the repair of osteochondral defects of the medical femoral condyle: a biomechanical and histological evaluation in the rabbit knee", *Biomaterials,* 14(7):513–521 (1993).

Bruns et al., "Autologous rib perichondrial grafts in experimentally induced osteochondral lesions in the sheep–knee joint: morphological results" *Virchows Archiv A Pathol Anat,* 421:1–8 (1992).

Thoma et al., "Perichondrial arthroplasty in a Canine Elbow Model: Comparison of Vascularized and Nonvascularized Techniques", *Plastic and Reconstructive Surgery,* 91(2):307–315 (1993).

von Schroeder et al., "The use of polylactic acid matrix and periosteal grafts for the reconstruction of rabbit knee articular defects", *Journal of Biomedical Materials Research,* 25:329–339 (1991).

Nakahara et al., "In Vitro Differentiation of Bone and Hypertrophic Cartilage from Periosteal–Derived Cells", *Experimental Cell Research,* 195:492–503 (1991).

Allard et al., "The Synovium–Cartilage Junction of the Normal Human Knee", *Arthritis and Rheumatism,* 33(8):1170–1179 (1990).

Sandberg et al., "In Suit Localization of Collagen Production by Chondrocytes and Osteoblasts in Fracture Callus", *The Journal of Bone and Joint Surgery,* 71–A(1):69–77 (1989).

O'Driscoll et al., "The Chondrogenic Potential of Free Autogenous Periosteal Grafts for Biological Resurfacing of Major Full–Thickness Defects in Joint Surfaces under the Influence of Continuous Passive Motion", *The Journal of Bone and Joint Surgery,* 68–A(7):1017–1035 (1986).

O'Driscoll et al., "Regenerated Articular Cartilage Produced by Free Periosteal Grafts: The Effects of CPM on its Long–Term Durability", *31st Annual ORS, Las Vega, Nevada,* p. 292 (Jan. 21–24, 1985).

Rubak et al., "Effects of Joint Motion on the Repair of Articular Cartilage With Free Periosteal Grafts", *Acta orthop. scand.,* 53:187–191 (1982).

J. M. Rubak, "Reconstruction of Articular Cartilage Defects with Free Periosteal Grafts", *Acta orthop. scand.,* 53:175–180 (1982).

METHOD FOR REPAIRING CARTILAGE

1. INTRODUCTION

The present invention relates to methods for making and/or repairing cartilage in vivo. More specifically, the invention relates to methods of making and/or repairing cartilage comprising implanting into a patient, at a site of cartilage damage or loss, a biocompatible, non-living three-dimensional scaffold or framework structure, in combination with periosteal/perichondrial tissue, and administering a preparation of chondrocytes and/or other stromal cells, such as chondrocyte progenitor cells, to the site of the implant before, during or after implantation of the scaffold and/or the periosteal/perichondrial tissue. The periosteal/perichondrial tissue can be used to hold the scaffold in place at the site of implantation and also provides a source of stromal cells, e.g., chondrocytes and/or chondrocyte progenitor cells, for attachment to the scaffold in vivo. The preparation of stromal cells seeded directly into the implantation site in vivo provides not only a readily-accessible source of chondrocytes and/or other stromal cells for attachment to the scaffold but also provides a rapid and efficient means of inducing chondrogenesis as well as migration of stromal cells from the surrounding in vivo environment to the scaffold via factors produced by the stromal cells of the preparation. Additionally, the seeded stromal cells can be genetically engineered to express gene products beneficial to growth, implantation and/or amelioration of disease conditions. The methods of the invention therefore result in the efficient production of new cartilage in vivo.

The methods of this invention are useful in the production/repair of articular cartilage in patients suffering from degenerative connective tissue diseases such as rheumatoid and/or osteoarthritis as well as in patients who have cartilage defects due to trauma. The methods of this invention can be used to replace or augment existing cartilage tissue, to introduce new or altered tissue or to join together biological tissues or structures.

2. BACKGROUND OF THE INVENTION

There are various types of cartilage, e.g., articular or hyaline cartilage, elastic cartilage and fibrocartilage. Articular cartilage is found at the articular surfaces of bones, e.g., in the joints, and is responsible for providing the smooth gliding motion characteristic of moveable joints. Articular cartilage is firmly attached to the underlying bones and measures less than 5mm in thickness in human joints, with considerable variation depending on joint and site within the joint. In addition, articular cartilage is aneural, avascular, and alymphatic. In adult humans, this cartilage derives its nutrition by a double diffusion system through the synovial membrane and through the dense matrix of the cartilage to reach the chondrocyte, the cells that are found in the connective tissue of cartilage.

In fact, articular cartilage consists of highly specialized chondrocyte cells surrounded by a dense extracellular matrix consisting mainly of type II collagen, proteoglycan and water. While the biochemical composition of articular cartilage includes up to 65–80% water (depending on the cartilage), the collagen component of the cartilage is the most prevalent organic constituent. The collagen (mainly type II) accounts for about 15–25% of the wet weight or about half the dry weight, except in the superficial zone where it accounts for most of the dry weight. Its concentration is usually progressively reduced with increasing depth from the articular surface. The proteoglycan content accounts for up to 10% of the wet weight or about a quarter of the dry weight. Proteoglycans consist of a protein core to which linear sulfated polysaccharides are attached, mostly in the form of chondroitin sulfate and keratin sulfate. In addition to type II collagen, articular collagen contains several other collagen types (IV, V, IX and X) with distinct structures. There are a variety of interactions between these individual macromolecules, which include both noncovalent associations between proteoglycans and collagens, and covalent bonds between different collagen species. Resistance of the extracellular matrix to water flow gives cartilage its ability to dispense high joint loads. It absorbs shock and minimizes stress on subchondral bone (Mow et al., 1984, J. Biomech. 17:377–394). However, adult cartilage and bone have a limited ability of repair; thus, damage to cartilage produced by disease, such as rheumatoid and/or osteoarthritis, or trauma can lead to serious physical deformity and debilitation. Furthermore, as human articular cartilage ages, its tensile properties change. The superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not decrease. These observations indicate that there are changes in mechanical and, hence, structural organization of cartilage with aging that, if sufficiently developed, can predispose cartilage to traumatic damage. In osteoarthritic cartilage, there is excessive damage to type II collagen, resulting in crimping of collagen fibrils. In rheumatoid arthritis, the combined actions of free radicals and proteinases released from polymorpholeukocytes cause much of the damage seen at the articular surface (Tiku et al., 1990, J. Immunol. 145:690–696). Induction of cartilage matrix degradation and proteinases by chondrocytes is probably induced primarily by interleukin-1 (IL-1) or tumor necrosis factor-$\alpha$ (TNF-$\alpha$) (Tyler, 1985, Biochem. J. 225:493–507).

The current therapy for damage or loss of cartilage is replacement with a prosthetic material, for example, silicone for cosmetic repairs, or metal alloys for joint realignment. Implantation of prosthetic devices is usually associated with loss of underlying tissue and bone without recovery of the full function allowed by the original cartilage. Serious long-term complications associated with the presence of a permanent foreign body can include infection, erosion and instability.

Use of sterilized bone or bone powder or surgical steel seeded with bone cells that are eventually implanted have been largely unsuccessful because of the non-degradable nature of the cell support. According to one procedure, fibroblasts are exposed in vitro for a minimum of three days to a soluble bone protein capable of stimulating a chondrogenic response. The activated fibroblasts are then transferred in vivo by combining them with a biodegradable matrix or by intra-articular injection or attachment to allografts or prosthetic devices. The disadvantage of this method is that chondrogenesis is not allowed to develop in the short-term cultures and there is an unduly heavy reliance on cartilage synthesis by the exposed fibroblasts at the implant site. See Caplan, A., U.S. Pat. No. 4,609,551, issued Sep. 2, 1986.

U.S. Pat. No. 5,041,138 to J. P. Vacanti et al., issued Aug. 20, 1991, describes the growth of cartilaginous structures by seeding chondrocytes on biodegradable matrices in vitro for subsequent implantation in vivo. U.S. Pat. Nos. 5,197,985 and 5,226,914, to Caplan et al., issued Mar. 30, 1993 and Jul. 13, 1993, respectively, relate to culturing marrow-derived mesenchymal stem cells in vitro in the presence of growth factors, applying these cells to a carrier, e.g., a porous ceramic vehicle, to promote round cell morphology, and implanting the carrier containing the cells into damaged articular cartilage. Finally, U.S. Pat. No. 4,520,821, to Schmidt et al., issued Jun. 4, 1985 relates to a method of growing a biological tissue correction structure using a bioabsorbable mesh or gauze. According to a preferred embodiment, biological tissue is removed from a defective area of the body and grown in vitro on a bioabsorbable mesh and the tissue/mesh structure is placed into the area of the defect in vivo for a time long enough to allow the mesh to be completely bioabsorbed. In all of the approaches cited above, cells are applied to a carrier in vitro for implantation into the site of a cartilage lesion.

U.S. Pat. No. 4,846,835 to Grande et al., issued Jul. 11, 1989, also describes a grafting technique for promoting articular cartilage healing by culturing autologous chondrocytes in vitro and seeding the chondrocytes on a collagen matrix in vitro. Grande further describes implanting the chondrocyte/collagen matrix into a cartilage lesion and mechanically fixing the graft by suturing a periosteal flap to the cartilage. Grande teaches that the periosteum has very little chondrogenic potential and that the periosteal flap utilized therein could have been substituted by a resorbable biocompatible polymer to achieve the same fixation purpose. While von Schroeder et al., 1991, J. Biomed. Mat. Res. 25:329–339, relates to periosteal grafts in combination with a polylactic acid matrix for the repair of full-thickness osteochondral defects in animals, Messner, 1994, Biomaterials 15 (No. 3): 223–230 describes experiments in which periosteal grafts in combination with Teflon and Dacron felts for the repair of full-thickness osteochondral defects were unsatisfactory in achieving normal cartilage repair in animals. O'Driscoll et al., 1986, J. Bone and Joint Surg. 68-A (No. 7): 1017–1035; O'Driscoll et al., 1985, 31st Annual ORS, p. 292, Las Vegas, Nev., Jan. 21–24, 1985; Rubak, 1982, Acta. Orthop. Scand. 53:175–180; and Messner et al., 1993, Biomaterials 14 (No. 7): 513–521 relate to the use of free autogenous periosteal grafts that are placed directly into full-thickness articular defects for the repair of such defects in animals.

In addition, Thoma et al., 1993, Plast. Reconstr. Surg. 91 (No. 2): 307–315 and Bruns et al., 1992, Virchows. Arch. A. Pathol. Anat. Histopathol. 421 (No. 1): 1–8 relate to the use of autogenous perichondrial grafts for the repair of full-thickness articular defects in animals. Thoma noted marked degenerative changes resembling osteoarthritis in the perichondrial grafts and concluded that spontaneous repair of such large defects may result in a more normal new articular cartilage than the perichondrial grafts attempted. Bruns noted hyaline-like cartilage in non-weight-bearing areas of the defect, but not in weight-bearing areas. Finally, Bean et al., 1994, ORL J. Otorhinolaryngol. Relat. Spec. 56:224–229 reports the use of a composite graft of demineralized bovine bone matrix and autogenous perichondrium for the reconstruction of the anterior laryngeal wall in rabbits.

3. SUMMARY OF THE INVENTION

The present invention relates to methods of making and/or repairing cartilage in vivo comprising implanting into a patient, at a site of cartilage damage or loss, a biocompatible, non-living three-dimensional scaffold or framework structure in combination with periosteal/perichondrial tissue that can be used to hold the scaffold in place and provides a source of chondrocyte progenitor cells, chondrocytes and other stromal cells for attachment to the scaffold in vivo. In addition, a preparation of cells that can include chondrocytes, chondrocyte progenitor cells or other stromal cells is administered, either before, during or after implantation of the scaffold and/or the periosteal/perichondrial tissue; the cells are administered directly into the site of the implant in vivo and promote chondrogenesis and the production of factors that induce the migration of chondrocytes, progenitor cells and other stromal cells from the adjacent in vivo environment into the scaffold for the production of new cartilage at the site of implantation.

More specifically, the three-dimensional scaffold contains interstitial spaces into which progenitor cells, chondrocytes and other stromal cells from the adjacent in vivo environment, including the implanted periosteal/perichondrial tissue, migrate for attachment and growth on and within the scaffold structure. The preparation of stromal cells seeded in combination with the scaffold and periosteal/perichondrial tissue provides a ready source of chondrocytes and other stromal cells which produce biological factors that promote chondrogenesis and the migration of stromal cells from, e.g., the periosteal/perichondrial tissue to the scaffold for attachment and/or differentiation thereon. The stromal cell preparation also provides a direct source of stromal cells, e.g., chondrocytes and/or progenitor cells, that are capable of migrating into the scaffold and attaching thereto. The stromal cells in the scaffold, whether derived from the periosteal/perichondrial tissue, from the exogenous stromal cell preparation or from the in vivo environment adjacent to the implant site, grow on the scaffold to form a cellular matrix and provide the support, growth factors and regulatory factors required for cartilage formation at a cartilage defect site in vivo. The methods of this invention thus result in the production of new cartilage in vivo at the implant site.

In a preferred embodiment of the methods of the invention, the periosteal/perichondrial tissue is placed over the implanted scaffold at the site of cartilage damage or loss ("the defect site") and affixed, e.g., by sutures, to that site, thus holding the scaffold in place. According to a further preferred embodiment, the scaffold is composed of a biodegradable material such that, upon successful engraftment, the scaffold structure is completely absorbed in vivo, resulting in new cartilage having no foreign, non-living material encompassed within it.

According to another preferred embodiment, the preparation of chondrocytes and/or other stromal cells is administered in vivo to the site of the implant after the scaffold and periosteal/perichondrial tissue have been implanted. In yet a further embodiment of the invention, bioactive agents such as cellular growth factors (e.g., TGF-$\beta$), factors that stimulate chondrogenesis (e.g., bone morphogenic proteins (BMPs) that promote cartilage formation), factors that stimulate migration of stromal cells and/or matrix deposition, anti-inflammatories or immunosuppressants, are included at the implantation site. For example, these factors can be incorporated into the scaffold material to provide for release at the site of implantation; the scaffold can also be comprised of, or coated with, one or more of these bioactive agents. Alternatively, the factor(s) can be administered into or adjacent to the scaffold, either before, during or after seeding of the stromal cells, e.g., the bioactive agent(s) can be administered to the site, either as a separate preparation or as part of the stromal cell preparation. In addition, the stromal cells seeded at the defect site can be genetically engineered to express the genes for these bioactive agents, e.g., specific types of TGF-$\beta$ such as TGF-$\beta$1 or specific types of BMPs such as BMP-13. Exposure of the defect site to these bioactive agents promotes the successful and/or improved production of new cartilage and/or improves the success of implantation, for example, by reducing the risk of rejection or inflammation associated with the implant.

For example, according to one embodiment of the invention, the stromal cells can be genetically engineered to express anti-inflammatory gene products to ameliorate the effects of degenerative diseases like rheumatoid arthritis which result in cartilage damage due to inflammatory reactions; e.g., the stromal cells can be engineered to express peptides or polypeptides corresponding to the idiotype of neutralizing antibodies for granulocyte-macrophage colony stimulating factor (GM-CSF), tumor necrosis factor (TNF), interleukin-2 (IL-2), or other inflammatory cytokines and mediators.

According to another embodiment, the stromal cells can be genetically engineered to express tissue factors that enhance migration of stromal cells from the adjacent in vivo environment into the scaffold at the implantation site.

Preferably, the cells are engineered to express such gene products transiently and/or under inducible control during the post-operative recovery period, or as a chimeric fusion protein anchored to the stromal cell, e.g., a chimeric molecule composed of an intracellular and/or transmembrane domain of a receptor or receptor-like molecule, fused to the gene product as the extracellular domain.

In another alternative embodiment, the stromal cells can be genetically engineered to "knock out" expression of factors that promote rejection of the implant or degenerative changes in articular cartilage due to aging, rheumatoid disease or inflammation. For example, expression of pro-inflammatory mediators such as GM-CSF, TNF, IL-1, IL-2 and cytokines can be knocked out in the exogenously-administered stromal cells or on the implanted periosteal or perichondrial tissue to reduce the risk of inflammation. Likewise, the expression of MHC class II molecules on the cells or tissues can be knocked out in order to reduce the risk of rejection of the implant.

In another embodiment of the invention, the methods of the invention may afford a vehicle for introducing genes and gene products in vivo to assist or improve the results of the implantation and/or for use in gene therapies. For example, genes that prevent or ameliorate symptoms of degenerative changes in cartilage such as rheumatoid disease or inflammatory reactions and bone resorption, may be underexpressed or overexpressed in disease conditions and/or due to aging. Thus, the level of gene activity in the patient may be increased or decreased, respectively, by gene replacement therapy by adjusting the level of the active gene product in genetically engineered stromal cells.

In yet another preferred embodiment, the cartilage defect site into which the implant will be placed is treated, preferably prior to implantation, to degrade the pre-existing cartilage at the defect site, freeing cells to migrate into the scaffold of the implant and promoting the orderly deposition of new cartilage. Methods of such treatment include enzymatic treatment, abrasion or microdrilling. According to a further embodiment, the preparation of stromal cells of the invention can be injected into the degraded cartilage at the defect site, e.g., into the surrounding cells or into the walls of the defect, providing a source of biological factors that induce migration of stromal cells from the degraded cartilage to the implant.

4. DETAILED DESCRIPTION OF THE INVENTION

The present invention involves methods of making and/or repairing cartilage in vivo comprising the implantation in vivo of a three-dimensional scaffold or framework structure made of a biocompatible, non-living material in combination with periosteal/perichondrial tissue and the administration of a preparation of stromal cells, such as chondrocytes or chondrocyte progenitor cells, which cells are seeded at the site of implantation in vivo.

The term "chondrocyte progenitor cell" as used herein refers to either (1) a pluripotent, or lineage-uncommitted, progenitor cell, typically referred to in the art as a "stem cell" or "mesenchymal stem cell", which is potentially capable of an unlimited number of mitotic divisions to either renew its line or to produce progeny cells which will differentiate into chondrocytes; or (2) a lineage-committed progenitor cell produced from the mitotic division of a stem cell which will eventually differentiate into a chondrocyte. Unlike the stem cell from which it is derived, the lineage-committed progenitor is generally considered to be incapable of an unlimited number of mitotic divisions and will eventually differentiate into a chondrocyte.

The term "cartilage" or "cartilage tissue" as used herein is generally recognized in the art, and refers to a specialized type of dense connective tissue comprising cells embedded in an extracellular matrix (ECM) (see, for example, Cormack, 1987, *Ham's Histology,* 9th Ed., J. B. Lippincott Co., pp. 266–272). The biochemical composition of cartilage differs according to type; however, the general composition of cartilage comprises chondrocytes surrounded by a dense ECM consisting of collagen, proteoglycans and water. Several types of cartilage are recognized in the art, including, for example, hyaline or articular cartilage such as that found within the joints, fibrous cartilage such as that found within the meniscus and costal regions, and elastic cartilage. The production of any type of cartilage is intended to fall within the scope of the invention.

Furthermore, although the invention is directed predominantly to methods for the production of new cartilage tissue in humans, the invention may also be practiced so as to produce new cartilage tissue in any mammal in need thereof, including horses, dogs, cats, sheep, pigs, among others. The treatment of such animals is intended to fall within the scope of the invention.

The invention is divided into the following sections solely for the purpose of description: (a) the three-dimensional scaffold; (b) the periosteal/perichondrial tissue and its implantation in combination with the scaffold; (c) the stromal cell preparation, including genetically engineered stromal cells; (d) administration of the stromal cells in vivo and (e) uses of the methods of the invention.

4.1. THE THREE-DIMENSIONAL SCAFFOLD

The three-dimensional scaffold or framework structure may be of any material and/or shape that: (a) allows cells to attach to it (or can be modified to allow the cells to attach to it); and (b) allows cells to grow in more than one layer. Because the three-dimensional structure is to be implanted in vivo, it may be preferable to use biodegradable materials such as polyglycolic acid (PGA), polylactic acid (PLA), hyaluronic acid, catgut suture material, gelatin, cellulose, nitrocellulose, collagen, cotton, or other naturally-occurring biodegradable materials. Furthermore, it may be preferable to sterilize the three-dimensional structure prior to implantation, e.g., by treatment with ethylene oxide or by gamma irradiation or irradiation with an electron beam.

In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), and a variety of polyhydroxyalkanoates. Because certain of these materials, such as nylon, polystyrene, etc. may be poor substrates for cellular attachment, when these materials are used as the three-dimensional framework, it is advisable to pre-treat the framework prior to implantation in order to enhance the attachment of chondrocytes and other stromal cells to the scaffold. For example, nylon matrices can be treated with 0.1 M acetic acid and incubated in polylysine, PBS, and/or collagen to coat the nylon. Polystyrene could be similarly treated using sulfuric acid.

Any of the above-listed materials may be formed into a mesh or a felt, for example, to produce the three-dimensional framework or scaffold for use in the methods of this invention. Regardless of the shape of the framework, the openings of the framework should be of an appropriate size to allow the chondrocytes and other stromal cells to stretch across the openings. Maintaining actively growing stromal cells which stretch across the framework enhances the production of growth factors which are elaborated by the stromal cells, and further enhances new cartilage formation in vivo. In addition, the openings of the framework must allow for adequate diffusion of nutrients and waste products into and out of the structure and for vascularization at the site of implantation. For example, if the openings are too small, the stromal cells may rapidly achieve confluence but be unable to easily exit from the matrix; trapped cells may exhibit contact inhibition and cease production of the appropriate factors necessary to support proliferation. If the openings are too large, the stromal cells may be unable to stretch across the opening; this will also decrease stromal cell production of the appropriate factors necessary to support proliferation. When using a mesh type of framework, openings ranging from about 150 µm to about 220 µm are satisfactory. However, depending upon the three-dimensional structure and intricacy of the framework, other sizes may work equally well. In fact, any shape or structure that allows the stromal cells to stretch and continue to replicate and grow for lengthy time periods will work in accordance with the invention. For example, for felt-type frameworks, openings ranging from about 80 µm to about 120 µm are preferred.

According to a preferred embodiment, the scaffold is a felt, which can be composed of a multifilament yarn made from a bioabsorbable material, e.g., PGA, PLA, polyglu-conate (PLGA) or hyaluronic acid. The yarn is made into a felt using standard textile processing techniques consisting of crimping, cutting, carding and needling. According to a further preferred embodiment, the porosity of the felt ranges from 80–98%, the density of the felt ranges from 30–60 mg/cc and the thickness of the felt ranges from 1–7 mm.

In an embodiment wherein the scaffold is made of collagen, the collagen may be in the form of a sponge, a braid or woven threads, etc. In an embodiment wherein the scaffold is made of nylon, a convenient nylon mesh is Nitex, a nylon filtration mesh having an average pore size of 210 µm and an average nylon fiber diameter of 90 µm (#3–210/36 Tetko, Inc., N.Y.).

Although Applicants are under no duty or obligation to explain the mechanism by which the invention works, a number of factors inherent in the three-dimensional framework may contribute to its successful use in the present invention:

(a) The three-dimensional framework provides a greater surface area for protein attachment, and consequently, for the adherence of stromal cells in vivo.

(b) Because of the three-dimensionality of the matrix, as noted above, the stromal cells that attach to the framework continue to actively grow and produce growth and regulatory factors which promote new cartilage formation in vivo, and are less likely to exhibit contact inhibition.

(c) The three-dimensional framework allows for a spatial distribution of cellular elements which is analogous to that found in vivo.

(d) The increase in potential volume for cell growth in the three-dimensional structure may allow the establishment of localized microenvironments conducive to cellular differentiation and maturation in the production of new cartilage in vivo.

(e) The three-dimensional matrix maximizes cell-cell interactions by allowing greater potential for movement of migratory cells, such as macrophages, monocytes and possibly lymphocytes.

(f) It has been recognized that maintenance of a differentiated cellular phenotype requires not only growth/differentiation factors but also the appropriate cellular interactions. The present invention effectively recreates the in vivo tissue microenvironment.

According to one embodiment of the invention, the scaffold may comprise or be modified, e.g., coated or impregnated, prior to implantation with certain substances to enhance the attachment and growth of chondrocytes and other stromal cells on the scaffold in vivo. These substances include, but are not limited to, bioactive agents such cellular growth factors (e.g., TGF-$\beta$), substances that stimulate chondrogenesis (e.g., BMPs that stimulate cartilage formation such as BMP-2, BMP-12 and BMP-13), factors that stimulate migration of stromal cells to the scaffold, factors that stimulate matrix deposition, anti-inflammatories (e.g., non-steroidal anti-inflammatories), immunosuppressants (e.g., cyclosporins), as well as other proteins, such as collagens, elastic fibers, reticular fibers, glycoproteins or glycosaminoglycans, such as heparin sulfate, chondroitin-4-sulfate, chondroitin-6-sulfate, dermatan sulfate, keratin sulfate, etc. For example, growth factors such as TGF-$\beta$, with ascorbate, have been found to trigger chondrocyte differentiation and cartilage formation by chondrocytes. In addition, hyaluronic acid is a good substrate for the attachment of chondrocytes and other stromal cells and can be incorporated as part of the scaffold or coated onto the scaffold.

These bioactive agents may also be included in or on the scaffold for local, sustained release of the agents. Examples of such sustained release formulations include composites comprising the bioactive agent and a biocompatible polymer, such as poly(lactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al., 1992, Polymers for Advanced Technologies 3:279–292. Additional guidance in selecting and using polymers in pharmaceutical formulations can be found in the text by M. Chasin and R. Langer (eds.), 1990, "Biodegradable Polymers as Drug Delivery Systems, Vol. 45 of *Drugs and the Pharmaceutical Sciences*, M. Dekker, New York.

4.2. THE PERIOSTEAL/PERICHONDRIAL TISSUE AND ITS IMPLANTATION IN COMBINATION WITH THE SCAFFOLD

The scaffold of the invention as described above is implanted into the defect site in vivo in combination with periosteal tissue, perichondrial tissue or a combination of the two tissues. Periosteal tissue is derived from the periosteum, a fibrous membrane localized at the surfaces of bones, and can be obtained from the periosteum/bone interface of any suitable bone of the patient (or subject) or a histocompatible donor, e.g., ileum, scapula, tibia, fibula, femur, etc. The periosteal tissue contains a variety of stromal cells including osteocytes, chondrocytes and fibroblasts as well as mesenchymal stem cells having the potential to differentiate into osteogenic or chondrogenic cells. Perichondrial tissue is derived from the perichondrium, the fibrous connective tissue covering cartilage, except articular surfaces. Perichondrial tissue contains chondrogenic progenitor cells and chondrocytes.

The periosteal/perichondrial tissue can be in the form of a segment or layer of tissue of any size or shape, preferably of a size and shape that fits within or corresponds to the defect site. The tissue can be laid over or under the scaffold at the implantation site and can optionally be mechanically fixed to the scaffold and/or the defect site, e.g., by sutures or glue fixation, e.g., fibrin glue. Although it may be preferable for the periosteal/perichondrial tissue to be autologous (i.e., derived from the subject receiving the implant), the tissue may be derived from a heterologous source. When periosteal/perichondrial tissue from a heterologous source is used, it may be preferable to add anti-inflammatory factors or immunosuppressants to the defect site, e.g., attached to or within the scaffold or exogenously administered to the site, to minimize the risk of immunological rejection.

According to a preferred embodiment of the invention, the three-dimensional scaffold is implanted at the defect site in vivo and a piece of periosteal/perichondrial tissue is placed over the implanted scaffold and sutured in place so that the tissue overlays and lies adjacent to the scaffold structure. Alternatively, a segment of periosteum or perichondrium may be implanted directly into the defect site and the scaffold placed on top of the tissue such that the stromal cells of the tissue can migrate from the tissue into the scaffold. In any case, the periosteal/perichondrial tissue should be situated with respect to the scaffold in such a way as to allow the stromal cells from the tissue to migrate into the scaffold and proliferate thereon and therein. The scaffold and/or periosteal/perichondrial tissue can be implanted using surgical techniques well known in the art, e.g., arthroscopy.

According to a preferred embodiment, the periosteal tissue is situated or oriented such that the cambium layer of the tissue is facing into the defect; thus, in the embodiment wherein the scaffold is placed directly into the defect site and the periosteal tissue is placed on top of the scaffold, the periosteal tissue is oriented in relation to the top of the scaffold such that the cambium layer is facing the top of the scaffold. When perichondrial tissue is used in the claimed methods, the perichondrial tissue is also placed into the defect site or oriented with respect to the scaffold such that its cambium or inner transition layers faces the defect or scaffold. It is these layers that contain chondrogenic stem cells and/or chondrocytes that can migrate into the scaffold for the production of new cartilage at the defect site.

In an alternative embodiment of the invention, a bioresorbable patch, e.g., film, mesh or felt, can be used in place of the periosteal/perichondrial tissue and situated or oriented adjacent to the scaffold within the defect site. For example, if a film is used, it may be comprised of PGA or polygluconate; if a mesh or felt is used, they may be comprised of vicryl or PLA. The preparation of stromal cells is seeded into the defect site as described herein.

According to a further embodiment of the invention, the defect site is treated, preferably prior to implantation, to degrade the cartilage at the site of the defect, freeing cells (e.g., stromal cells) from that area to migrate into the scaffold of the implant and promoting the orderly deposition of new cartilage. When enzymes are used to treat the defect site, such enzymes include but are not limited to trypsin, chymotrypsin, collagenase, elastase, and/or hyaluronidase, Dnase, pronase, chondroitinase, etc.

Alternative methods of treating the defect site to degrade the cartilage include abrasion, debridement, shaving or microdrilling. Where abrasion techniques are utilized, the surface of the cartilage may be serrated, e.g., via wire wool. In microdrilling, a drilling device is used to create small defects or channels in the cartilage. Treatment of the defect site to degrade or disrupt the pre-existing cartilage reduces the chances of scar tissue forming at the site and promotes the orderly deposition of new cartilage at the defect site.

4.3. THE STROMAL CELL PREPARATION

According to the methods of this invention, a preparation of stromal cells is additionally administered at the implantation site, which cells produce biological factors that promote chondrogenesis and the migration of cells such as chondrogenic stem cells or chondrocytes, from the in vivo environment adjacent to the implant, including from the periosteal/perichondrial tissue, to the scaffold for attachment and/or differentiation thereon and therein. The stromal cell preparation also provides a direct source of stromal cells, e.g., chondrocytes and/or chondrocyte progenitor cells, that are capable of migrating to the scaffold, attaching thereto, and elaborating cartilage-specific macromolecules and extracellular matrix proteins for the production of new cartilage at the defect site. The cells described herein can be administered before, during or after implantation of the scaffold and/or periosteal/perichondrial tissue, as discussed in Section 4.4, infra.

The stromal cells of the preparation may include chondrocytes, chondrocyte progenitor cells including mesenchymal stem cells, fibroblasts, fibroblast-like cells and/or cells capable of producing collagen type II and other collagen types, and proteoglycans which are typically produced in cartilaginous tissues. The stromal cells can be obtained from the patient (or subject) or a histocompatible donor. The chondrocytes, progenitor cells, fibroblast-like cells and other cells and/or elements that comprise the stroma may be fetal or adult in origin, and may be derived from convenient sources such as cartilage, bone, skin, ligaments, tendons, muscles, placenta, umbilical cord, etc. For example, stromal cells such as chondrocytes may be derived from any type of cartilage, including but not limited to, hyaline cartilage, costal cartilage, fibrous cartilage, etc., which can be obtained by biopsy (where appropriate) or upon autopsy. Chondrocyte progenitor cells may be derived from various sources including bone marrow, periosteum, perichondrium or various sources of undifferentiated human mesenchyme. Fibroblasts can be obtained in quantity rather conveniently from foreskin, preferably fetal foreskin, or, alternatively, any appropriate cadaver organ. Fetal cells, including fibroblast-like cells and chondrocyte progenitor cells, may be obtained from umbilical cord or placenta tissue or umbilical cord blood. Although stromal cells from a variety of sources may be used in the claimed methods, it is preferable that, for implantation in vivo, the stromal cells be derived from the individual who is to receive the implant or from cells of fetal origin which may be viewed as "universal donors" so as to minimize the risk of immunological rejection of the implant.

The stromal cells may be readily isolated by disaggregating an appropriate tissue which is to serve as the source of the cells. This may be readily accomplished using techniques known to those skilled in the art. For example, the tissue can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, Dnase, pronase, etc. Mechanical disruption can also be accomplished by a number of methods including, but not limited to the use of grinders, blenders, sieves, homogenizers, pressure cells, or sonicators to name but a few. For a review of tissue disaggregation techniques, see Freshney, *Culture of Animal Cells. A Manual of Basic Technique,* 2d Ed., A. R. Liss, Inc., New York, 1987, Ch. 9, pp. 107–126.

Once the tissue has been reduced to a suspension of individual cells, the suspension can be fractionated into subpopulations from which chondrocytes, fibroblasts and/or other stromal cells and/or elements can be obtained. This also may be accomplished using standard techniques for cell separation including but not limited to cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, counter current distribution, electrophoresis and fluorescence-activated cell sorting. For a review of clonal selection and cell separation techniques, see Freshney, supra, Ch. 11 and 12, pp. 137–168.

For example, the isolation of chondrocytes, chondrocyte progenitors, fibroblasts or fibroblast-like cells is carried out as follows: fresh human cartilage tissue can be thoroughly washed and minced in Hanks balanced salt solution (HBSS) in order to remove serum. The minced tissue is incubated from 1–12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated stromal cells can then be grown to confluency, lifted from the confluent culture and administered to the cartilage defect site in vivo (see, e.g., Naughton et al., 1987, J. Med. 18(3&4):219–250). Fibroblast-like cells may also be isolated from human umbilical cords (33–44 weeks). Fresh tissues may be minced into pieces and washed with medium or snap-frozen in liquid nitrogen until further use. The umbilical tissues may be disaggregated as described above.

Once chondrocytes or chondrocyte progenitor cells have been isolated, their population can be expanded mitotically in vitro in order to obtain the cell preparation for implantation. Methods for the selection of the most appropriate culture medium, medium preparation, and cell culture techniques are well known in the art and are described in a variety of sources, including Doyle et al., (eds.), 1995, *Cell & Tissue Culture: Laboratory Procedures*, John Wiley & Sons, Chichester; and Ho and Wang (eds.), 1991, *Animal Cell Bioreactors*, Butterworth-Heinemann, Boston.

The cells should be transferred or "passaged" to fresh medium when they reach an appropriate density, such as 3 to $6.5 \times 10^4/cm^2$, or, for example, when they reach a defined percentage of confluency on the surface of a culture dish. During incubation, the stromal cells may stick to the walls of the culture vessel where they can continue to proliferate and form a confluent monolayer. This should be prevented or minimized, for example, by transferring a portion of the cells to a new culture vessel having fresh medium, since the presence of a confluent monolayer in the culture vessel will tend to "shut down" the growth of cells in the culture. Removal of the confluent monolayer or transfer of a portion of the cells to fresh media in a new vessel will usually restore proliferative activity of the cells. Such removal or transfer should be done in any culture vessel which has a monolayer exceeding about 25% confluency. Alternatively, the liquid culture can be agitated, for example, on an orbital shaker or in roller bottles, to prevent or minimize the cells from sticking to the vessel walls.

In addition, once the stromal cells have been established in culture, they may be maintained or stored in cell "banks" comprising either continuous in vitro cultures of cells requiring regular transfer, or, preferably, cells which have been cryopreserved. Cryopreservation of the cells may be carried out according to known methods, such as those described in Doyle et al., 1995, supra. For example, but not by way of limitation, cells may be suspended in a "freeze medium" such as, for example, culture medium further comprising 20% FBS and 9% dimethylsulfoxide (DMSO), with or without 5–10% glycerol, at a density, for example, of about $4–10 \times 10^6$ cells/ml. The cells are dispensed into glass or plastic ampoules (Nunc) which are then sealed and transferred to the freezing chamber of a programmable freezer. The optimal rate of freezing may be determined empirically. For example, a freezing program that gives a change in temperature of $-1°$ C./min through the heat of fusion may be used. Once the ampoules have reached $-180°$ C., they are transferred to a liquid nitrogen storage area. Cryopreserved cells can be stored for a period of years, though they should be checked at least every 5 years for maintenance of viability.

The cryopreserved cells constitute a bank of cells, portions of which can be "withdrawn" by thawing and then used to produce new cartilage tissue as needed. Thawing should generally be carried out rapidly, for example, by transferring an ampoule from liquid nitrogen to a 37° C. water bath. The thawed contents of the ampoule should be immediately transferred under sterile conditions to a culture vessel containing an appropriate medium such as RPMI 1640 conditioned with 10% FBS and 5% ES. It is advisable that the cells in the culture medium be adjusted to an initial density of about $3–6 \times 10^5$ cells/ml so that the cells can condition the medium as soon as possible, thereby preventing a protracted lag phase. Once in culture, the cells may be examined daily, for example, with an inverted microscope to detect cell proliferation, and subcultured as soon as they reach an appropriate density.

In addition to chondrocytes, chondrocyte progenitors, fibroblasts or fibroblast-like cells, other cells may be added to the cell preparation for implantation in vivo, which other cells aid in the production of the stromal matrix on the scaffold of the invention. For example, other cells found in loose connective tissue may be seeded along with chondrocytes or fibroblasts. Such cells include but are not limited to endothelial cells, pericytes, macrophages, monocytes, plasma cells, mast cells, adipocytes, etc. These stromal cells may readily be derived from appropriate organs including umbilical cord or placenta or umbilical cord blood using methods known in the art such as those discussed above.

Moreover, the stromal cell preparation may further comprise one or more other components, including selected extracellular matrix components, such as one or more types of collagen known in the art, as well as growth factors and/or drugs. Growth factors which may be usefully incorporated into the cell preparation include one or more tissue growth or stimulatory factors known in the art or to be identified in the future, including but not limited to any member of the TGF-β family, BMPs that stimulate cartilage formation, e.g., BMP-2, BMP-12, and BMP-13, factors that stimulate migration of stromal cells and/or matrix deposition, insulin-like growth factor (IGF)-I and -II, growth hormone, etc. Drugs which may be usefully incorporated into the cell preparation include anti-inflammatory compounds such as non-steroidal anti-inflammatories, immunosuppressants such as the cyclosporins, as well as local anesthetics. Other components may also be included in the preparation, including but not limited to any of the following: (1) buffers to provide appropriate pH and isotonicity; (2) lubricants; (3) viscous materials to retain the cells at or near the site of administration, including, for example, alginates, agars and plant gums; and (4) other cell types that may produce a desired effect at the site of administration, such as, for example, enhancement or modification of the formation of cartilage tissue or its physicochemical characteristics, or support for the viability of the cells, or inhibition of inflammation or rejection.

Again, because the cells are to be used for implantation in vivo, it is preferable to obtain the stromal cells from the patient's own tissues or from a fetal source ("universal donor"). The growth of cells on the three-dimensional scaffold may be further enhanced by including in or on the framework or coating the framework with proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), and/or other bioactive materials such as growth factors.

According to one embodiment of the invention, growth regulatory or stimulatory factors including, but not limited to, TGF-β and ascorbate, or BMPs that stimulate cartilage formation such as BMP-2, BMP-12, and BMP-13 may be added to the implantation site before, during or after implantation of either the scaffold and/or the periosteal/perichondrial tissue, in order to promote the production of new cartilage at the site. Moreover, such growth regulatory factors can be administered to the site at the time of administration of the stromal cells, either as a separate preparation or, as noted supra, as part of the stromal cell preparation.

In addition, the stromal cells may be genetically engineered to produce growth factors such as TGF-β as well as other biological factors such as factors that stimulate chondrogenesis or the migration of chondrogenic and other stromal cells to the scaffold of this invention.

4.3.1. GENETICALLY ENGINEERED STROMAL CELLS

The stromal cells administered to or in combination with the scaffold and periosteal/perichondrial tissue of the invention can also be genetically engineered to produce gene products that promote the successful production or repair of cartilage at a defect site and/or for use in gene therapies. For example, the stromal cells can be genetically engineered to express anti-inflammatory factors, e.g., anti-GM-CSF, anti-TNF, anti-IL-1, anti-IL-2, etc., to reduce the risk of rejection of the implant or to reduce the risk of degenerative changes in the cartilage due to rheumatoid disease or other inflammatory reactions. For example, the stromal cells can be genetically engineered to express peptides or polypeptides corresponding to the idiotype of neutralizing antibodies for granulocyte-macrophage colony stimulating factor (GM-CSF), TNF, IL-1, IL-2, or other inflammatory cytokines. IL-1 has been shown to decrease the synthesis of proteoglycans and collagens type II, IX, and XI (Tyler et al., 1985, Biochem. J. 227:869–878; Tyler et al., 1988, Coll. Relat. Res. 82:393–405; Goldring et al., 1988, J. Clin. Invest. 82:2026–2037; and Lefebvre et al., 1990, Biophys. Acta. 1052:366–372) and is a potent stimulator of cartilage resorption and of the production of inflammatory mediators by chondrocytes (Campbell et al., 1991, J. Immunol. 147:1238–1246). TNF also inhibits synthesis of proteoglycans and type II collagen, although it is much less potent than IL-1 (Yaron, I., et al., 1989, Arthritis Rheum. 32:173–180; Ikebe, T., et al., 1988, J. Immunol. 140:827–831; and Saklatvala, J., 1986, Nature 322:547–549).

Once the genetically engineered stromal cells are implanted into an individual, the presence of the anti-inflammatory gene products can bring about amelioration of immunological rejection or the inflammatory reactions associated with rheumatoid or joint disease.

In another embodiment, the stromal cells can be genetically engineered to express a gene which would exert a therapeutic effect, e.g., in the production of TGF-β to stimulate cartilage production, or other factors such as BMP-13 to promote chondrogenesis and/or prevent bone formation or stimulatory factors that promote migration of stromal cells and/or matrix deposition.

In addition, the stromal cells can be genetically engineered to express a gene for which a patent is deficient. For example, genes that prevent or ameliorate symptoms of various types of rheumatoid or joint diseases may be under-expressed or down-regulated under disease conditions. Specifically, expression of genes involved in preventing inflammatory reactions in rheumatoid or joint diseases may be down-regulated. Alternatively, the activity of gene products may be diminished, leading to the manifestations of some or all of the above pathological conditions and eventual development of symptoms of rheumatoid or joint diseases. Thus, the level of gene activity may be increased by either increasing the level of gene product present or by increasing the level of the active gene product present at the defect site. By implanting stromal cells genetically engineered to express the active target gene product into the defect site of a rheumatoid or joint disease patient who is deficient for that product, the level of the target gene product and/or the activity of that product can be modulated to prevent or ameliorate the symptoms of rheumatoid or joint diseases. "Target gene," as used herein, refers to a gene involved in rheumatoid or joint diseases in a manner by which modulation of the level of target gene expression or of target gene product activity may act to ameliorate symptoms of rheumatoid or joint diseases by preventing resorption of cartilage and production of inflammatory mediators by chondrocytes.

In addition, patients may be treated by gene replacement therapy by means of the stromal cells administered according to the methods of this invention. Thus, replacement or repaired cartilage may be designed specifically to meet the requirements of an individual patient; for example, the stromal cells may be genetically engineered to regulate one or more genes; or the regulation of gene expression may be transient or long-term; or the gene activity may be non-inducible or inducible. For example, the gene encoding the human complement regulatory protein, which prevents rejection of an implant by the host, may be inserted into human fibroblasts. McCurry et al., 1995, Nature Medicine 1:423–427.

The stromal cells used in the methods of the invention can also be genetically engineered to "knock out" expression of factors that promote inflammation or rejection at the implant site. Negative modulatory techniques for the reduction of target gene expression levels or target gene product activity levels are discussed below. "Negative modulation", as used herein, refers to a reduction in the level and/or activity of target gene product relative to the level and/or activity of the target gene product in the absence of the modulatory treatment. The expression of a gene native to stromal cell can be reduced or knocked out using a number of techniques, for example, expression may be inhibited by inactivating the gene completely (commonly termed "knockout") using standard homologous recombination techniques. Usually, an exon encoding an important region of the protein (or an exon 5' to that region) is interrupted by a positive selectable marker (for example neo), preventing the production of normal mRNA from the target gene and resulting in inactivation of the gene. A gene may also be inactivated by creating a deletion in part of a gene, or by deleting the entire gene. By using a construct with two regions of homology to the target gene that are far apart in the genome, the sequences intervening the two regions can be deleted. Mombaerts et al., 1991, Proc. Nat. Acad. Sci. U.S.A. 88:3084–3087.

Antisense and ribozyme molecules which inhibit expression of the target gene can also be used in accordance with the invention to reduce the level of target gene activity. For example, antisense RNA molecules which inhibit the expression of major histocompatibility gene complexes (HLA) have been shown to be most versatile with respect to immune responses. Furthermore, appropriate ribozyme molecules can be designed as described, e.g., by Haseloff et al., 1988, Nature 334:585–591; Zaug et al., 1984, Science 224:574–578; and Zaug and Cech, 1986, Science 231:470–475. Still further, triple helix molecules can be utilized in reducing the level of target gene activity. These techniques are described in detail by L.G. Davis et al., eds, *Basic Methods in Molecular Biology,* 2nd ed., Appleton & Lange, Norwalk, Conn. 1994.

Using any of the foregoing techniques, the expression of IL-1 can be knocked out in the chondrocytes to reduce the risk of resorption of cartilage and production of inflammatory mediators by the chondrocytes. Likewise, the expression of MHC class II molecules can be knocked out in order to reduce the risk of rejection of the implant.

Methods that may be useful to genetically engineer the cells of the invention are well-known in the art. For example, a recombinant DNA construct or vector containing the gene of interest may be constructed and used to transform or transfect the stromal cells of the invention. Such transformed or transfected cells that carry the gene of interest, and that are capable of expressing said gene, are selected and clonally expanded in culture. Methods for preparing DNA constructs containing the gene of interest, for transforming or transfecting cells, and for selecting cells carrying and expressing the gene of interest are well-known in the art. See, for example, the techniques described in Maniatis et al., 1989, *Molecular Cloning, A Laboratory Manual,* Cold Spring Harbor Laboratory Press, Cold Spring Harbor, N.Y.; Ausubel et al., 1989, *Current Protocols in Molecular Biology,* Greene Publishing Associates & Wiley Interscience, N.Y.; and Sambrook et al., 1989, *Molecular Cloning: A Laboratory Manual,* 2nd Ed., Cold Spring Harbor Laboratory Press, Cold Spring Harbor, N.Y.

The cells can be engineered using any of a variety of vectors including, but not limited to, integrating viral vectors, e.g., retrovirus vector or adeno-associated viral vectors; or non-integrating replicating vectors, e.g., papilloma virus vectors, SV40 vectors, adenoviral vectors; or replication-defective viral vectors. Where transient expression is desired, non-integrating vectors and replication defective vectors may be preferred, since either inducible or constitutive promoters can be used in these systems to control expression of the gene of interest. Alternatively, integrating vectors can be used to obtain transient expression, provided the gene of interest is controlled by an inducible promoter. Other methods of introducing DNA into cells include the use of liposomes, lipofection, electroporation, a particle gun, or by direct DNA injection.

Hosts cells are preferably transformed or transfected with DNA controlled by, i.e., in operative association with, one or more appropriate expression control elements such as promoter or enhancer sequences, transcription terminators, polyadenylation sites, among others, and a selectable marker. Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines. This method can be advantageously used to engineer cell lines which express the gene product.

Any promoter may be used to drive the expression of the inserted gene. For example, viral promoters include but are not limited to the CMV promoter/enhancer, SV40, papillomavirus, Epstein-Barr virus, elastin gene promoter and β-globin. Preferably, the control elements used to control expression of the gene of interest should allow for the regulated expression of the gene so that the product is synthesized only when needed in vivo. If transient expression is desired, constitutive promoters are preferably used in a non-integrating and/or replication-defective vector. Alternatively, inducible promoters could be used to drive the expression of the inserted gene when necessary. Inducible promoters can be built into integrating and/or replicating vectors. For example, inducible promoters include, but are not limited to, metallothionien and heat shock protein.

A variety of methods may be used to obtain the constitutive or transient expression of gene products engineered into the stromal cells. For example, the transkaryotic implantation technique described by Seldon et al., 1987, Science 236:714–718 can be used. "Transkaryotic", as used herein, suggests that the nuclei of the implanted cells have been altered by the addition of DNA sequences by stable or transient transfection. Preferably, the stromal cells are engineered to express such gene products transiently and/or under inducible control during the post-operative recovery period, or as a chimeric fusion protein anchored to the stromal cells, for example, as a chimeric molecule composed of an intracellular and/or transmembrane domain of a receptor or receptor-like molecule, fused to the gene product as the extracellular domain.

Once the stromal cells have been genetically engineered, they may be administered to the patient to produce new cartilage in cases of degenerative connective tissue disease or trauma.

4.4. ADMINISTRATION OF THE STROMAL CELLS IN VIVO

The preparation of stromal cells can be administered either before, during or after implantation of the scaffold and/or the periosteal/perichondrial tissue. For example, the cells can be seeded into the defect site before implantation of either the scaffold or the periosteal/perichondrial tissue. Alternatively, the stromal cells can be administered to the site after either one or both of the scaffold and tissue have been implanted; e.g., by injection into the site after suturing the periosteal/perichondrial tissue to the scaffold. According to a preferred embodiment, the cells are seeded between the periosteal/perichondrial tissue and the scaffold at the defect site. According to another preferred embodiment, the cells are seeded directly into the scaffold. In the embodiment of the invention wherein the cartilage at the defect site is treated so as to degrade the cartilage, the stromal cells can also be seeded into the degraded cartilage, e.g., into the surrounding cells or directly into the cartilage wall. The stromal cells act therein to induce the migration of stromal cells from the degraded cartilage to the implant.

The stromal cells can be seeded by any means that allows administration of the cells to the defect site, e.g., by injection. When the cells are injected into the site, such injection can be achieved by any means that maintains the viability of the cells, e.g., via syringe or more preferably, via an arthroscope. According to a preferred embodiment of the invention, the number of cells administered can range from approximately $1 \times 10^6$ to $30 \times 10^6$ stromal cells.

After the scaffold, periosteal/perichondrial tissue and stromal cells are implanted, the defect site is surgically sealed. According to a preferred embodiment of the invention, the stromal cells to be seeded are surgically obtained from the patient, e.g., from ear cartilage and/or bone marrow, in a separate surgical procedure, cultured in vitro to obtain an appropriate amount of cells and administered to the patient at the time of a second surgery wherein the scaffold and periosteal/perichondrial tissue are implanted. The periosteal/perichondrial tissue is preferably surgically obtained from the patient at the time that the scaffold is implanted, although the tissue can be cultured in vitro prior to implantation (see, e.g., O'Driscoll et al., 1994, J. Bone and Joint Surg. 76-A:1042–1051).

According to the methods of this invention, the stromal cells from the periosteal/perichondrial tissue and from the added stromal preparation populate the scaffold structure to form a stromal matrix that resembles the in vivo microenvironment of cartilage tissue, allowing for the production of new cartilage at the defect site. The stromal cells administered to the site provide important biological factors that promote chondrogenesis and the migration of stromal cells, whether from the implanted tissue, the in vivo cartilage environment of the defect or from the stromal preparation, to the scaffold, thus promoting the production of a living stromal tissue that provides the support, growth factors, and regulatory factors necessary to sustain long-term active proliferation of the stromal cells in vivo. The stromal cells may additionally provide factors that promote the deposition of the living stromal matrix at the defect site. The proliferating cells mature and segregate properly within the matrix to form new cartilage tissue at the defect site in vivo.

The successful repair or replacement of damaged cartilage can be enhanced if the new cartilage tissue can be fixed in place at the site of repair. Post-implantation movement may cause the new cartilage tissue to become dislodged from the site if a pro-active fixation technique is not employed. Various methods can be used to fix the new cartilage tissue in place, including: patches derived from a bioresorbable polymer or biocompatible tissues, which can be placed over the site and sutured; bioabsorbable sutures or other fasteners, e.g., pins, staples, tacks, screws, anchors, glues, e.g., fibrin glue; non-absorbable fixation devices, e.g., sutures, pins, screws and anchors; adhesives; and the use of interference fit geometries.

4.5. USES OF THE METHODS OF THE INVENTION

The methods of this invention are useful to replace or augment existing cartilage tissue in vivo, to introduce new or altered cartilage tissue or to join together biological tissues or structures. The present methods find use in a number of specific areas. For example, the evaluation of internal derangements of articular cartilage in several articulations, including the knee, hip, elbow, ankle and the glenohumeral joint, has been made possible by arthroscopic techniques. Such derangements can be caused by physical trauma to the cartilage, by various connective tissues diseases and/or by increased age of the individual. Arthroscopic surgery has become increasingly popular as well as successful, e.g., numerous small cutting tools, 3 to 4mm in diameter can be used in the knee. Triangulation, in which the operating instruments are brought into the visual field provided by the arthroscope, requires multiple portals of entry; alternatively, the cutting tools can be passed through a channel in the arthroscope itself in which case only one opening in the joint is necessary (Jackson, R. W., 1983, J. Bone Joint Surg. [AM] 65:416). Selective removal of damaged or deteriorated cartilage via arthroscopic surgery results in cartilage loss, which can be repaired using the methods of the present invention. The present methods can also be employed to repair or augment cartilage loss that results from major reconstructive surgery for different types of joints, the procedures for which surgery have been described in Resnick, D., and Niwayama, G., eds., 1988, *Diagnosis of Bone and Joint Disorders,* 2d ed., W.B. Sanders Co. Furthermore, the present methods are useful for reconstruction of the temporal mandibular joint as well as for other facial and cranial reconstructions.

As such, the present invention is useful for the production or repair of cartilage in vivo in the treatment of degenerative connective tissue diseases, such as rheumatoid or osteoarthritis, or in the treatment of physical trauma, wherein cartilage is damaged or lost.

5. EXAMPLE

The subsections below describe the components to be used in the methods of this invention as well as the in vivo implantation of a scaffold, periosteal tissue and stromal cells at a cartilage defect site according to the methods of the invention.

5.1. PREPARATION OF THREE-DIMENSIONAL SCAFFOLD

A three-dimensional scaffold comprising felt derived from a PGA multifilament yarn was generated. The yarn is commercially available from Davis and Geck/Sherwood Medical under the trade name Dexon™. The particular type of Dexon™ yarn is 56/123. The Dexon™ yarn is processed into felt via standard textile processing techniques. The felt sheet, which has a porosity of 97%, a density of 45 mg/cc and a thickness of 2–7 mm after processing, is cut into the appropriate size for implantation in vivo. Standard serialization techniques (radiation or ethylene oxide gas) for medical products are used to sterilize the felt. The felt can be implanted dry or pre-soaked using DMEM medium containing 10% fetal bovine serum, 2 mM L-glutamine, non-essential amino acids, 50 mg/ml proline, 1 mM sodium pyruvate, 35 µg/ml gentamicin sulfate and 50 µg/ml ascorbate.

5.2. PREPARATION OF PERIOSTEAL/ PERICHONDRIAL TISSUE

Periosteal tissue to be used in the methods of this invention is obtained by removing, e.g., by arthroscopy, a section of periosteum from the tibia or femur of the patient. Perichondrial tissue can be obtained by removing a section of the perichondrium from the rib of the patient. The periosteal/ perichondrial tissue is of such size and/or shape so as to correspond to the defect site. The excision of the periosteal/ perichondrial tissue from the patient is preferably performed at the time of the implantation of the scaffold.

5.3. PREPARATION OF STROMAL CELL PREPARATION

A preparation of human chondrocytes is obtained as described in Brittberg et al., 1994, New Eng. J. Med. 331 (No. 14): 890–895. For example, cartilage slices (e.g., 300–500 mg by weight) can be obtained by arthroscopy from a minor load-bearing area of a joint such as the femoral condyle of the knee. The cartilage tissue is placed in a chilled sterile solution of sodium chloride (0.9 % weight per volume) and cells are harvested within 2–5 hr by mincing and washing in Ham's F12 medium (Gibco Labs, Grand Island, N.Y.) containing HEPES buffer (10 mmol/l), gentamicin sulfate (50 $\mu$g/ml), amphotericin B (2 $\mu$g/ml), and L-ascorbic acid (50 $\mu$g/ml). The cells can similarly be harvested using the complete DMEM medium described in Section 5.1, supra. The cartilage is then digested with collagenase (0.2% weight/volume) for approximately 16 hr and the cells are filtered through a nylon mesh, washed with medium and resuspended in medium supplemented with the patient's serum. The cells are seeded at a density of approximately $1 \times 10^6$ cells per T-150 flask and cultured in an incubator at 37° C., 5% $CO_2$. Cells are passed at confluence every 5–7 days.

In addition, chondrocyte progenitor cells can be obtained using methods similar to those described in Wakitani et al., 1994, J. Bone and Joint Surg. 76-A (No. 4): 579–592. Briefly, blood is aspirated from bone marrow and the aspirate is washed and centrifuged at 180×g for 5 min. After resuspension in Ham's F12 medium supplemented with 10% FCS and antibiotics, the red blood cells are disrupted by treatment with 4% acetic acid and the remaining cells are cultured in complete medium (10% FCS) at 37° C. in a humidified atmosphere, 5% $CO_2$. At day 5, the medium is changed, which removes essentially all of the non-adherent cells. The adherent cells are grown as a monolayer until confluence. The cells are then trypsinized (0.25% trypsin, 1 mM EDTA) for 5 min, to release the cells from the culture dish.

Chondrocyte progenitor cells can also be obtained from periosteum harvested, e.g., from the tibia or femur. The periosteal tissue is incubated with 0.25% collagenase in Ham's F12 medium for 3 h at 37° C., applying periodic agitation. The tissue is then disrupted by vortexing and the cells are filtered through a 100-micrometer Nitex filter, washed twice and centrifuged. The cells are then cultured in complete medium, which is replaced every other day. Adherent cells are grown to confluence and released with trypsin as described above for the bone-marrow derived cells.

Prior to administration in vivo, the stromal cell preparation is suspended by treatment with trypsin, centrifuged and the pellet washed in culture medium supplemented with autologous serum. The cell preparation is then aspirated into a 1 ml tuberculin syringe with a 1.2 mm needle for administration to the implant site.

5.4. IMPLANTATION OF SCAFFOLD, PERIOSTEAL TISSUE AND STROMAL CELLS IN VIVO

The cartilage defect site is cleaned/sterilized prior to implantation by scrubbing or rinsing with a sterilizing solution, e.g., iodine surgical scrub, e.g., 0.75% titratable iodine, or 0.9% sodium chloride solution. The defect site can also be enzymatically treated to degrade the cartilage surface area of the defect by treatment with trypsin in the range of 0.1–100 Units/ml for 1–30 min depending upon the concentration of enzyme used.

The felt scaffold as described above, tailored to fit the defect site, is placed into the site and the periosteal tissue as described above is placed on top of the felt scaffold with the cambium layer of the periosteum facing toward the scaffold and into the defect. The periosteal tissue may optionally be sewn onto the ends of the felt scaffold using resorbable vicryl sutures. The flap is also sutured to the surrounding cartilage at the defect site.

Either prior to implantation of the scaffold and/or the periosteal tissue, the stromal cells of the preparation described above can be administered, e.g., by an arthroscope, into the defect site. For a defect 5 mm thick and 1.5 cm in diameter, a total of $14 \times 10^6$ stromal cells in 200 $\mu$l of a nutrient-based solution such as DMEM (with or without serum) is administered. According to a preferred embodiment, the stromal cells are injected between the periosteal tissue and the scaffold. The defect site is closed in layers with sutures and the site bandaged. A post-surgical analgesic may be administered.

The present invention is not to be limited in scope by the specific embodiments described which are intended as single illustrations of individual aspects of the invention, and functionally equivalent methods and components are within the scope of the invention, in addition to those shown and described herein will become apparent to those skilled in the art from the foregoing description. Such modifications are intended to fall within the scope of the appended claims.

What is claimed is:

1. A method of producing cartilage at a cartilage defect site in vivo comprising:
   (a) implanting into the defect site a biocompatible, non-living three-dimensional scaffold structure in combination with periosteal tissue, perichondrial tissue or a combination of said tissues; and
   (b) separately administering into the defect site a preparation of stromal cells for attachment to the scaffold in vivo and for inducing chondrogenesis or migration of stromal cells from the in vivo environment adjacent to the defect site to the scaffold.

2. The method of claim 1, wherein the scaffold is implanted into the defect site and the periosteal or perichondrial tissue is placed on top of and adjacent to the scaffold.

3. The method of claim 1, wherein the periosteal or perichondrial tissue is implanted into the defect site and the scaffold is placed on top of and adjacent to the tissue.

4. The method of claim 1, wherein the periosteal or perichondrial tissue is situated with respect to the scaffold such that stromal cells from the tissue can migrate from the tissue to the scaffold.

5. The method of claim 1, wherein the periosteal tissue is situated with respect to the scaffold such that the cambium layer of the tissue faces the scaffold.

6. The method of claim 1, wherein the perichondrial tissue is situated with respect to the scaffold such that the cambium or inner transition layers of the tissue face the scaffold.

7. The method of claim 1, wherein the preparation of stromal cells is administered prior to, during or after implantation of the scaffold structure.

8. The method of claim 1, wherein the preparation of stromal cells is administered prior to, during or after implantation of the periosteal or perichondrial tissue.

9. The method of claim 1, wherein the preparation of stromal cells is physically placed between the scaffold and the periosteal or perichondrial tissue.

10. The method of claim 1, wherein the scaffold structure is composed of a biodegradable material.

11. The method of claim 10, wherein the biodegradable material is polyglycolic acid, polylactic acid, cat gut sutures, cellulose, nitrocellulose, gelatin, collagen or polyhydroxyalkanoates.

12. The method of claim 1, wherein the scaffold structure is composed of a non-biodegradable material.

13. The method of claim 12, wherein the non-biodegradable material is a polyamide, a polyester, a polystyrene, a polypropylene, a polyacrylate, a polyvinyl, a polycarbonate, a polytetrafluorethylene, polyhydroxylakanoate, cotton or a cellulose.

14. The method of claim 1, wherein the scaffold is a felt.

15. The method of claim 1, wherein the scaffold is a mesh.

16. The method of claim 1, wherein the scaffold is treated with ethylene oxide prior to implantation.

17. The method of claim 1, wherein the scaffold is treated with an electron beam prior to implantation.

18. The method of claim 1, wherein the scaffold comprises or is modified to contain at least one substance capable of enhancing the attachment or growth of stromal cells on the scaffold.

19. The method of claim 18, wherein the substance is a bioactive agent selected from the group consisting of cellular growth factors, factors that stimulate migration of stromal cells, factors that stimulate chondrogenesis, factors that stimulate matrix deposition, anti-inflammatories, and immunosuppressants.

20. The method of claim 19, wherein the bioactive agent is a transforming growth factor-beta.

21. The method of claim 19, wherein the bioactive agent is a bone morphogenetic protein that stimulates cartilage formation.

22. The method of claim 19, wherein the bioactive agent further comprises a sustained release formulation.

23. The method of claim 22 further comprising a biocompatible polymer which forms a composite with the bioactive agent.

24. The method of claim 23, wherein the biocompatible polymer is selected from the group consisting of polylactic acid, poly(lactic-co-glycolic acid), methylcellulose, hyaluronic acid, and collagen.

25. The method of claim 18, wherein the substance is selected from the group consisting of collagens, elastic fibers, reticular fibers, heparin sulfate, chondroitin-4-sulfate, chondroitin-6-sulfate, dermatan sulfate, keratin sulfate and hyaluronic acid.

26. The method of claim 1, further comprising the step of administering to the defect site at least one substance capable of enhancing the attachment or growth of stromal cells on the scaffold.

27. The method of claim 26, wherein the substance is a bioactive agent selected from the group consisting of cellular growth factors, factors that stimulate migration of stromal cells, factors that stimulate chondrogenesis, factors that stimulate chondrogenesis, factors that stimulate matrix deposition, anti-inflammatories, and immunosuppressants.

28. The method of claim 27, wherein the substance is a transforming growth factor-beta.

29. The method of claim 27, wherein the bioactive agent is a bone morphogenetic protein that stimulates cartilage formation.

30. The method of claim 1, wherein the periosteal or perichondrial tissue is autologous to the defect site.

31. The method of claim 1, wherein the preparation of stromal cells comprises chondrocytes.

32. The method of claim 1, wherein the preparation of stromal cells comprises chondrocyte progenitor cells.

33. The method of claim 1, wherein the preparation of stromal cells comprises fibroblasts or fibroblast-like cells.

34. The method of claim 1, wherein the preparation of stromal cells comprises a combination of cells selected from the group consisting of chondrocytes, chondrocyte progenitor cells, fibroblasts, fibroblast-like cells, endothelial cells, pericytes, macrophages, monocytes, leukocytes, plasma cells, mast cells, adipocytes, umbilical cord cells, and bone marrow cells from umbilical cord blood.

35. The method of claim 1, wherein the preparation of stromal cells comprises at least one bioactive agent.

36. The method of claim 35, wherein the bioactive agent is selected from the group consisting of cellular growth factors, factors that stimulate migration of stromal cells, factors that stimulate chondrogenesis, factors that stimulate matrix deposition, anti-inflammatories, and immunosuppressants.

37. The method of claim 36, wherein the bioactive agent is a transforming growth factor-beta.

38. The method of claim 36, wherein the bioactive agent is a bone morphogenetic protein that stimulates cartilage formation.

39. The method of claim 1, wherein the stromal cells of the preparation are genetically engineered to produce at least one bioactive agent.

40. The method of claim 39, wherein the bioactive agent is selected from the group consisting of cellular growth factors, factors that stimulate migration of stromal cells, factors that stimulate chondrogenesis, factors that stimulate matrix deposition, anti-inflammatories, and immunosuppressants.

41. The method of claim 1, wherein the stromal cells of the preparation are genetically engineered to express a gene that is deficiently expressed in vivo.

42. The method of claim 1, wherein the stromal cells of the preparation are genetically engineered to prevent or reduce the expression of a gene expressed by the stromal cells.

43. The method of claim 1, wherein the cartilage defect site is treated to degrade the existing cartilage at the site.

44. The method of claim 43, wherein the treatment is selected from the group consisting of enzyme treatment, abrasion, debridement, shaving, and microdrilling.

45. The method of claim 44, wherein the enzyme treatment utilizes at least one enzyme selected from the group consisting of trypsin, chymotrypsin, collagenase, elastase, hyaluronidase, DNAase, pronase and chondroitinase.

46. The method of claim 43, wherein the cartilage defect site is enzymatically treated prior to implantation of the scaffold or the periosteal or perichondrial tissue.

47. The method of claim 32 or 34 wherein the chondrocyte progenitor cells comprise mesenchymal stem cells.

48. The method of claim 19, 27 or 36 wherein the bioactive agent is transforming growth factor-beta in combination with ascorbate.

* * * * *